(12) United States Patent
Weber et al.

(10) Patent No.: US 7,172,624 B2
(45) Date of Patent: Feb. 6, 2007

(54) MEDICAL DEVICE WITH MAGNETIC RESONANCE VISIBILITY ENHANCING STRUCTURE

(75) Inventors: Jan Weber, Maple Grove, MN (US); Lixiao Wang, Medina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 132 days.

(21) Appl. No.: 10/359,970

(22) Filed: Feb. 6, 2003

(65) Prior Publication Data

US 2004/0158310 A1 Aug. 12, 2004

(51) Int. Cl.
*A61F 2/06* (2006.01)
*A61B 5/05* (2006.01)

(52) U.S. Cl. ............... 623/1.16; 623/1.34; 623/1.46; 600/414; 600/420

(58) Field of Classification Search ......... 623/1.15, 623/1.16, 1.34, 1.46; 600/414, 420
See application file for complete search history.

(56) References Cited

U.S. PATENT DOCUMENTS

| | | | |
|---|---|---|---|
| 4,572,198 A | 2/1986 | Codrington | 128/653 |
| 4,706,670 A | 11/1987 | Andersen et al. | 128/344 |
| 5,041,126 A | 8/1991 | Gianturco | 606/195 |
| 5,160,890 A | 11/1992 | Roschmann | 324/314 |
| 5,170,789 A | 12/1992 | Narayan et al. | 128/653.5 |
| 5,271,400 A | 12/1993 | Dumoulin et al. | 128/653.2 |
| 5,307,808 A | 5/1994 | Dumoulin et al. | 128/653.2 |
| 5,445,151 A | 8/1995 | Darrow et al. | 128/653.3 |
| 5,447,156 A | 9/1995 | Dumoulin et al. | 128/653.2 |
| 5,699,801 A | 12/1997 | Atalar et al. | 128/653.2 |
| 5,728,079 A | 3/1998 | Weber et al. | 604/280 |
| 5,738,632 A | 4/1998 | Karaswa | 600/410 |
| 5,744,958 A | 4/1998 | Werne | 324/318 |
| 5,755,781 A | 5/1998 | Jayaraman | 623/1 |
| 5,843,120 A | 12/1998 | Israel et al. | 606/198 |
| 5,916,264 A | 6/1999 | Von Oepen et al. | 623/1 |
| 5,922,020 A | 7/1999 | Klein et al. | 623/1 |
| 5,938,601 A | 8/1999 | Young | 600/411 |
| 5,951,494 A | 9/1999 | Wang et al. | 600/585 |
| 5,964,705 A | 10/1999 | Truwit et al. | 600/423 |
| 6,042,588 A | 3/2000 | Munsinger et al. | 606/108 |
| 6,093,157 A | 7/2000 | Chandrasekaran | 600/585 |

(Continued)

FOREIGN PATENT DOCUMENTS

EP 0 240 504 B1 11/1990

(Continued)

OTHER PUBLICATIONS

U.S. Appl. No. 10/670,433, filed Sep. 24, 2003, Weber.

(Continued)

*Primary Examiner*—Corrine McDermott
*Assistant Examiner*—Thomas Sweet
(74) *Attorney, Agent, or Firm*—Fish & Richardson P.C.

(57) ABSTRACT

A medical device that inhibits distortion of medical resonance images taken of the device. In particular, various structures are utilized to allow visibility proximate, and inside of, a tubular member, such as a stent. In one embodiment, the stent does not contain electrically conductive loops. In an alternative embodiment, rings in the stent are arranged such that current in one ring portion is opposed by current in another ring portion.

20 Claims, 7 Drawing Sheets

U.S. PATENT DOCUMENTS

| | | | | |
|---|---|---|---|---|
| 6,168,621 | B1 | 1/2001 | Vrba | 623/1.2 |
| 6,171,240 | B1 | 1/2001 | Young et al. | 600/410 |
| 6,174,329 | B1 | 1/2001 | Callol et al. | 623/1.34 |
| 6,231,516 | B1 | 5/2001 | Keilman et al. | 600/485 |
| 6,241,760 | B1 | 6/2001 | Jang | 623/1.12 |
| 6,251,086 | B1 | 6/2001 | Cornelius et al. | 600/585 |
| 6,258,071 | B1 | 7/2001 | Brookes | 604/272 |
| 6,263,229 | B1 | 7/2001 | Atalar et al. | 600/423 |
| 6,280,385 | B1 * | 8/2001 | Melzer et al. | 600/423 |
| 6,334,870 | B1 | 1/2002 | Her et al. | 623/1.16 |
| 6,340,367 | B1 | 1/2002 | Stinson et al. | 623/1.34 |
| 6,409,754 | B1 | 6/2002 | Smith et al. | 623/1.16 |
| 6,416,538 | B1 | 7/2002 | Ley et al. | 623/1.15 |
| 6,463,317 | B1 | 10/2002 | Kucharczyk et al. | 600/411 |
| 6,475,168 | B1 | 11/2002 | Pugsley, Jr. et al. | 600/585 |
| 6,487,437 | B1 | 11/2002 | Wiswanathan et al. | 600/423 |
| 6,537,310 | B1 | 3/2003 | Palmaz et al. | 623/1.13 |
| 6,585,755 | B2 | 7/2003 | Jackson et al. | 623/1.15 |
| 6,585,763 | B1 | 7/2003 | Keilman et al. | 623/1.42 |
| 6,767,360 | B1 * | 7/2004 | Alt et al. | 623/1.15 |
| 2002/0183829 | A1 | 12/2002 | Doscher et al. | 623/1.15 |
| 2002/0188345 | A1 | 12/2002 | Pacetti et al. | 623/1.15 |

FOREIGN PATENT DOCUMENTS

| | | |
|---|---|---|
| EP | 0 824 900 A2 | 2/1998 |
| WO | WO 93/13825 | 7/1993 |
| WO | WO 96/26689 | 9/1996 |
| WO | WO 00/12147 | 3/2000 |
| WO | WO 01/08600 A2 | 2/2001 |
| WO | WO 02/30331 A1 | 4/2002 |
| WO | WO 02/053066 A1 | 11/2002 |
| WO | WO 03/075792 A2 | 9/2003 |

OTHER PUBLICATIONS

Dieter Stockel, "Nitinol-Material with Unusual Properties", NDC, A Johnson & Johnson Company.

N. W. Cheung et al., "Plasma Immersion Ion Implantation for Electronic Materials Applications", Extended Abstracts of the 1995 International Conference on Solid State Devices and Materials, Osaka, 1995, pp. 351-353.

Shana Behnke, "An Examination of Nitinol Properties in Correlation with Their Use in Vascular Grafts", Materials Science and Engineering, University of Wisconsin, Apr. 27, 2001.

Mantese et al., "Plasma-Immersion Ion implantation", MRS Bulletin, Aug. 1996. pp. 52-56.

Zeng et al., "Influence of Sample Placement on the Dose Uniformity in Plasma Immersion Ion Implantation of Industrial Ball Bearings", IEEE Transactions on Plasma Science, vol. 27, No. 4, Aug. 1999, pp. 1203-1209.

En et al., "Plasma Immersion Ion Implantation Reactor Design Considerations for Oxide Charging", Surface and Coatings Technology 85, 1996, pp. 64-69.

Steam Turbine Technology Brochure, "Plasma Immersion Ion Processing", pp. 1-3, htt://www.swri.edu/3pubs/brochure/d18/plasma/plasma.htm.

Terashima et al., "High Resolution Real-Time and Color-Flow MRI of Nitinol Stents", Proc. Intl. Soc. Mag. Reson.Med. 10, 2002.

Xiao-Yan Gong et al., "ABACUS Analysis on Nitinol Medical Applications", 2002 ABACUS Users' Conference, pp. 1-10.

"Plasma Immersion ion Implantation for the Treatment of Metal Surfaces", Session RFI-Plasma Surface Interactions, FOCUS Session, Oct. 8, http://eee.eps.org/aps/meet/GEC99/baps/abs/S62005.html.

Copy of International application as republished on Dec. 2, 2004, for PCT/US2004/003274.

International Preliminary Report on Patentability, Aug. 25, 2005.

* cited by examiner

MEDICAL DEVICE WITH MAGNETIC RESONANCE VISIBILITY ENHANCING STRUCTURE

BACKGROUND OF THE INVENTION

The present invention relates generally to devices for use in vascular treatments. More particularly the present invention relates to devices used in vascular. treatments that incorporate a magnetic resonance visibility enhancing structure, the devices being adapted for use in magnetic resonance imaging.

Vascular stents are known medical devices used in various vascular treatments of patients. Stents commonly include a tubular member that is moveable from a collapsed, low profile, delivery configuration to an expanded, deployed configuration. In the expanded configuration, an outer periphery of the stent frictionally engages an inner periphery of a lumen. The deployed stent then maintains the lumen such that it is substantially unoccluded and flow therethrough is substantially unrestricted. However, various stent designs render the stent substantially invisible during a Magnetic Resonance Imaging procedure.

Magnetic Resonance Imaging, (MRI) is a non-invasive medical procedure that utilizes magnets and radio waves to produce a picture of the inside of a body. An MRI scanner is capable of producing pictures of the inside of a body without exposing the body to ionizing radiation (X-rays). In addition, MRI scans can see through bone and provide detailed pictures of soft body tissues.

A typical MRI scanner includes a magnet that is utilized to create a strong homogeneous magnetic field. A patient is placed into or proximate the magnet. The magnetic field causes a small majority of the atoms with a net magnetic moment, also referred to as spin, to align in the same direction as the magnetic field. When a radiowave is directed at the patient's body, atoms precessing in the magnetic field with a frequency equal to the radiowave are able to adapt the radiowave energy, which causes them to "tumble over" and align in the opposite direction of the magnetic field. The frequency at which atoms with a net spin precess in a magnetic field is also referred to as the Larmor frequency. The opposing alignment is at a higher energy level compared to the original orientation. Therefore, after removing the radiowave, atoms will return to the lower energetic state. As the atoms return to the lower energetic state, a radio signal is sent at the Lamor frequency. These return radio waves create signals (resonance signals) that are detected by the scanner at numerous angles around the patient's body. The signals are sent to a computer that processes the information. and compiles an image or images. Typically, although not necessarily, the images are in the form of 2-dimensional "slice" images.

An ability to effectively view areas proximate a stent during an MRI procedure is desirable. In particular, viewing areas inside and proximate a tubular member of a stent may be desirable both during deployment and after deployment of the stent in a patient. However, various current stent designs prevent adequate imaging of the area surrounding the stent. Instead, the images are distorted and thus cannot be used.

SUMMARY OF THE INVENTION

Embodiments of the present invention relate to medical devices that reduce the distortion of medical resonance images taken of the devices. In particular, various structures are utilized to enhance visibility proximate and inside of a tubular member of a stent. In one particular embodiment, the stent does not contain electrically conductive loops. In another embodiment, ring portions in the stent are arranged such that current in one ring portion is opposed by current in another connected ring portion.

DETAILED DESCRIPTION OF ILLUSTRATIVE EMBODIMENTS

Figure 1:
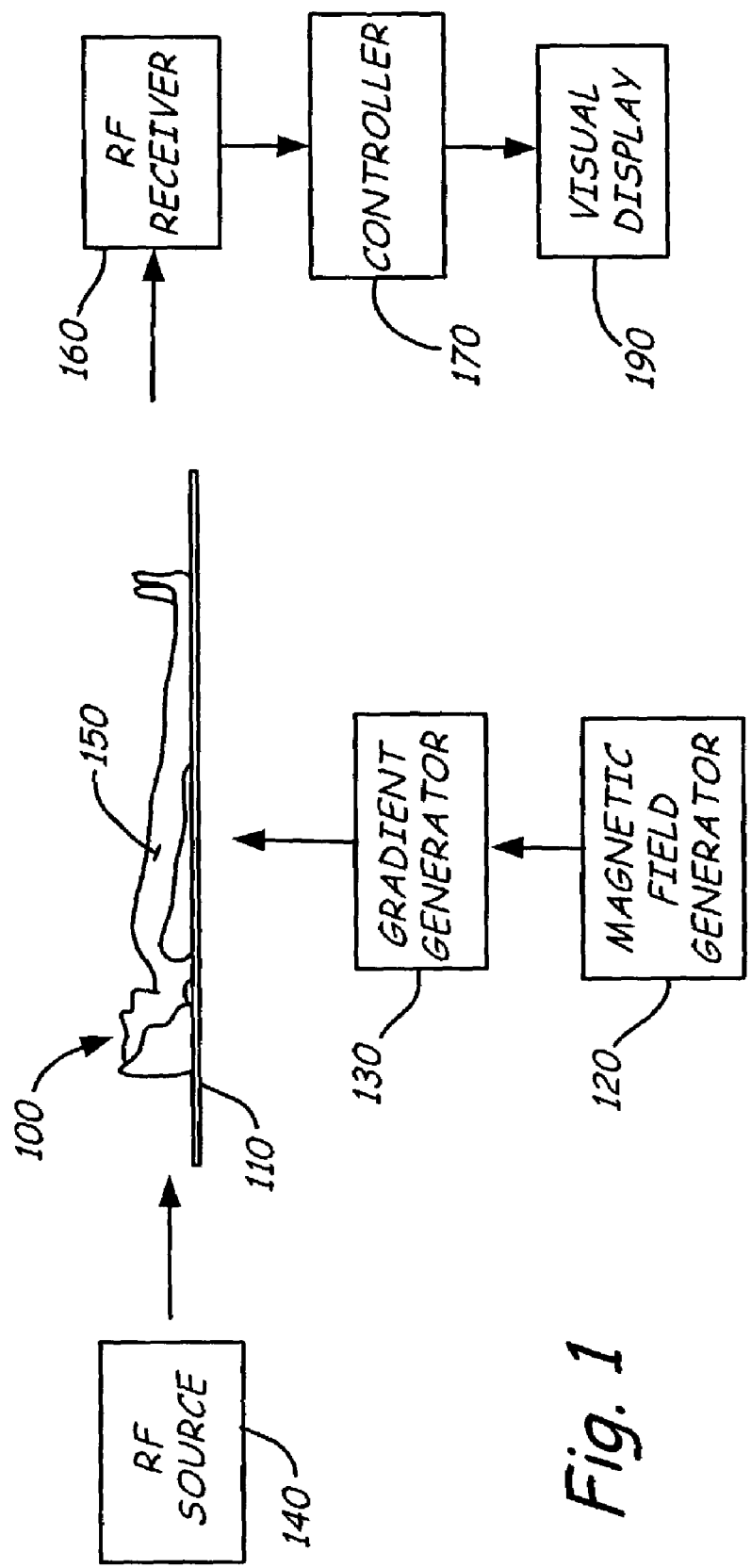
FIG. 1 is a partial block diagram of an illustrative magnetic resonance imaging system.

FIG. 1 is a partial block diagram of an illustrative magnetic resonance imaging system. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a stent, has been inserted, is located in the body of subject 100.

RF source 140 radiates pulsed radio frequency energy into subject 100 and stent 150 at predetermined times and with sufficient power at a predetermined frequency to influence nuclear magnetic spins in a fashion known to those skilled in the art. The influence on the atoms causes them to resonate at the Larmor frequency. The Larmor frequency for each spin is directly proportional to the absolute value of the magnetic field experienced by the atom. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass, the entire subject 100. Other geometries, such as smaller cylinders specifically designed for imaging the head or an extremity can be used instead. Non-cylindrical external coils such as surface coils may alternatively be used.

External RF receiver 160 illustratively detects RF signals emitted by the subject in response to the radio frequency field created by RF source 140. In an illustrative embodiment, external RF receiver 160 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils, such as surface coils, may alternatively be used. External RF receiver 160 can share some or all of its structure with RF source 140 or can have a structure entirely independent of RF source 140. The region of sensitivity of RF receiver 160 is larger than that of the stent 150 and can encompass the entire subject 100 or a specific region of subject 100. The RF signals detected by external RF receiver 160 are sent to imaging and tracking controller unit 170 where they are analyzed. Controller 170 displays signals received by RF receiver 160 on visual display 190.

Establishing a homogenous, or uniform, magnetic field with magnetic field generator 120 in addition to switched linear gradient magnetic fields activated in various sequences as well as timely switching the RF radiowave in various sequences, as known in the art, enables the production of internal images of subject 100. It is common that the magnetic field surrounding stent 150 is distorted, which causes distortion of images obtained proximate stent 150. This is because devices that include ferromagnetic materials will generally distort magnetic fields. For example, it is common for the material and structure of stent 150 to affect the magnetic field around stent 150. Such effects reduce the influence that magnetic field generator 120, gradient generator 130 and RF source 140 have on the nuclear magnetic spins in subject 100. In particular, the spins inside a tubular member of a stent are commonly not excited during an MRI and thus no image is detected.

One embodiment of the present invention includes using non-ferromagnetic materials in stent 150 to reduce this distortion. Such materials include, by way of example, platinum, iridium, tantalum, titanium, gold, niobium, hafnium alloys exhibiting non-ferromagnetic properties, and other non-ferromagnetic materials. Combinations of non-ferromagnetic materials can also be utilized without departing from the scope of the present invention. Another effect that commonly distorts the magnetic field around an intravascular device is associated with Faraday's Law. Faraday's Law simply states that any change in a magnetic environment of a coil will cause a voltage (emf) to be "induced" in the coil. Stent 150 can act as a coil when implanted in a subject during an MDRI process. The change in magnetic environment is caused either by stent 150 moving within a magnetic field, or by changes in the magnetic field proximate stent 150. For example, stent 150 may move due to the heart beating or magnetic field changes may be induced by gradient generator 130 or RF Source 140.

According to Faraday's Law, the induced emf in a coil is equal to the negative of the rate of change of magnetic flux through the coil times the number of turns in the coil. When an emf is generated by a change in magnetic flux, the polarity of the induced emf produces a current creating a magnetic field that opposes the change which produces it. Accordingly, the induced magnetic field inside any loop of wire acts to keep the magnetic flux inside the loop constant.

Figure 2:
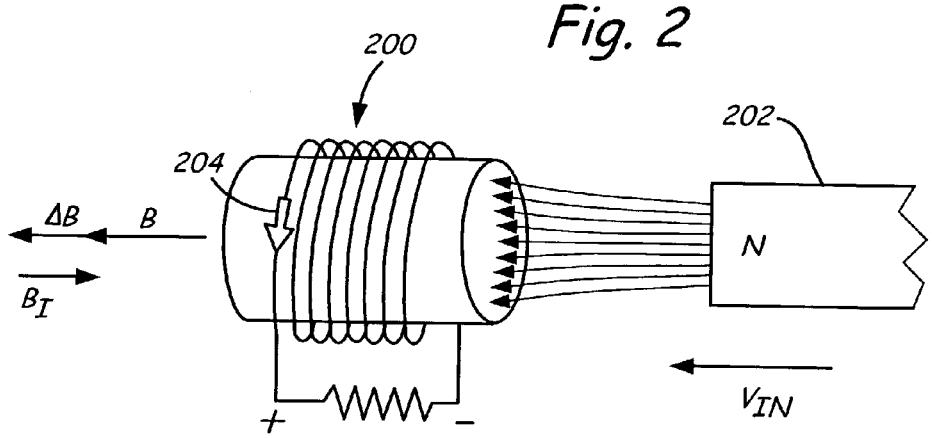
FIG. 2 is an illustration of a coil in a changing magnetic field.

FIG. 2 further illustrates this effect. Coil 200 has been placed in a magnetic field produced by magnet 202. The magnetic field is represented by a vector B. Any change in magnetic field B, herein represented as $\Delta B$, causes a current, represented as arrow 204, to be produced in coil 200. Current 204 causes a magnetic field $B_I$ to be induced, which opposes the change $\Delta B$.

When attempting to produce an image of stent 150 inside subject 100, the stent acts as a coil or, depending on the structure of the stent, as multiple coils. During various phases of an MRI process to influence the nuclear spins, a change in the magnetic field inside the stent is generated. For example, gradient generator 130 may generate a pulse in order to influence spins to be analyzed by controller 170. The gradient generator 130 thus changes the magnetic field and accordingly a change in magnetic field proximate the stent is opposed by Faraday's Law. As a result, spins proximate the stent are not excited and images of the stent show a lack of signal.

In order to reduce the effect of Faraday's Law on spins inside the stent, various stent designs have been made in accordance with embodiments of the present invention. In one embodiment, the creation of electrical loops within a stent structure is avoided. In yet another embodiment, a structure is used wherein current moving in one direction is opposed by a parallel current moving in the opposite direction. Using these designs, the visibility of a stent during an MRI process is enhanced.

Figure 3A:
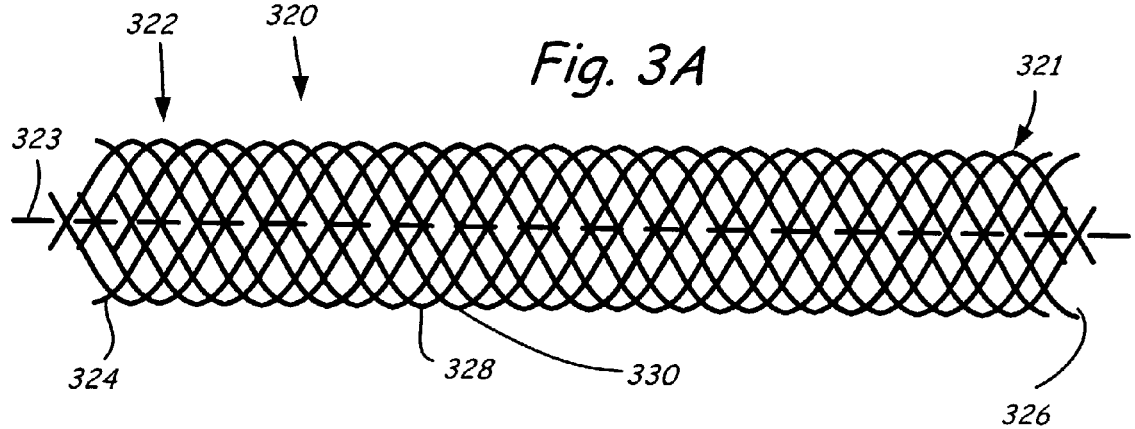
FIG. 3A is a side perspective view of a stent.

Stent 320 is illustrated in FIG. 3A according to one embodiment of the present invention. Stent 320 includes a plurality of bands or rings 322, wrapped around a central axis 323 to form a generally tubular structure 321. Rings 322 can be made of a material that is substantially non-ferromagnetic. Illustratively, rings 322 are equally spaced about axis 323 and flexible to allow bending of tubular structure 321. The flexibility of tubular structure 321 allows stent 320 to be placed in various lumens of different shapes and sizes. Rings 322 frictionally engage an inner periphery of a lumen when tubular structure 321 is open to allow fluid flow therethrough. Each of the rings 322 extend axially from a first end 324 of the stent 320 to a second end 326 of the stent 320 and terminate at each end to prevent the formation of electrical loops.

An insulating material has been applied to each of rings 322 prior to assembly of the tubular structure 321. The insulating material could be applied to rings 322 in various ways, such as coating and depositing, for example. Thus, each of the rings 322 is spaced apart from the others by the insulating material. Accordingly, each of the rings 322 is electrically insulated from each other ring in order to prevent electrical loops from forming in tubular structure 321. Various insulating materials may be used including, as examples, polymeric and ceramic materials. As appreciated by those skilled in the art, other stent structures such as mesh or woven structures may also be used.

Figure 3B:
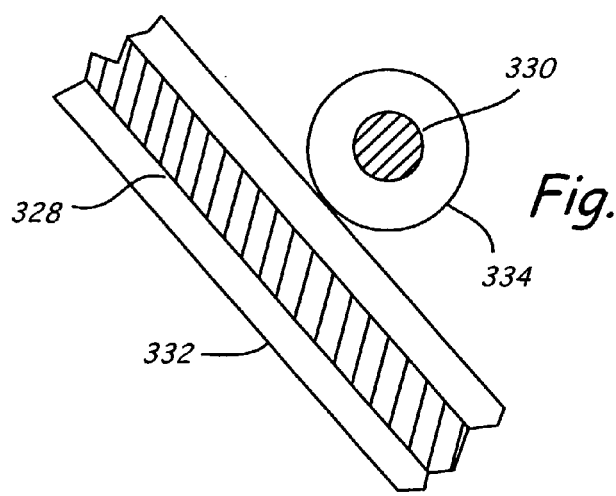
FIG. 3B is a cross-section of the stent illustrated in FIG. 3A.

As illustrated, various rings 322 of tubular structure 321 intersect at an angle to form a braided structure. For example, rings 328 and 330 intersect at an angle. FIG. 3B illustrates a cross section of an intersection between rings 328 and 330. At the point of intersection, insulating material 332 coating ring 328 engages insulating material 334 coating ring 330. Thus, rings 328 and 330 are electrically insulated from each other and spaced apart by their respective insulating materials.

Figure 3C:
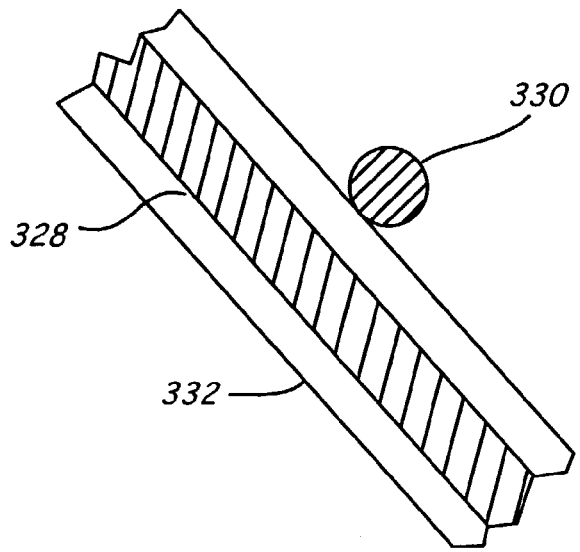
FIG. 3C is an alternative embodiment of a portion of a cross-section of the stent illustrated in FIG. 3A.

It will be appreciated that not all of the rings in a stent need to be coated with an insulating material. The insulating material is only needed to prevent any electrically conducting loops. For example, coating may be applied to only one of the rings at an intersection point with another ring. Additionally, intersecting rings may be made of differing materials, such as ring 328 being electrically conductive and ring 330 made of an insulating material. FIG. 3C illustrates an intersection point wherein a ring 330 contacts insulating material 332 coated over ring 328. Ring 330 does not include an insulating coating. The coating of insulating material needs only to be present at the point of intersection and may be applied prior to or after assembly of rings 328 and 330. In one embodiment, a heat shrink tube comprised of polytetrafluoroethylene (PTFE) is used to coat one of the rings. It will further be appreciated that the coating does not have to encompass the total circumference of the ring, but only a section of the ring in order to avoid electrical contact between two rings. For example, a flat wire may be coated with insulating material on one side, wherein the side with the insulating coating intersects with another ring.

Figure 4:
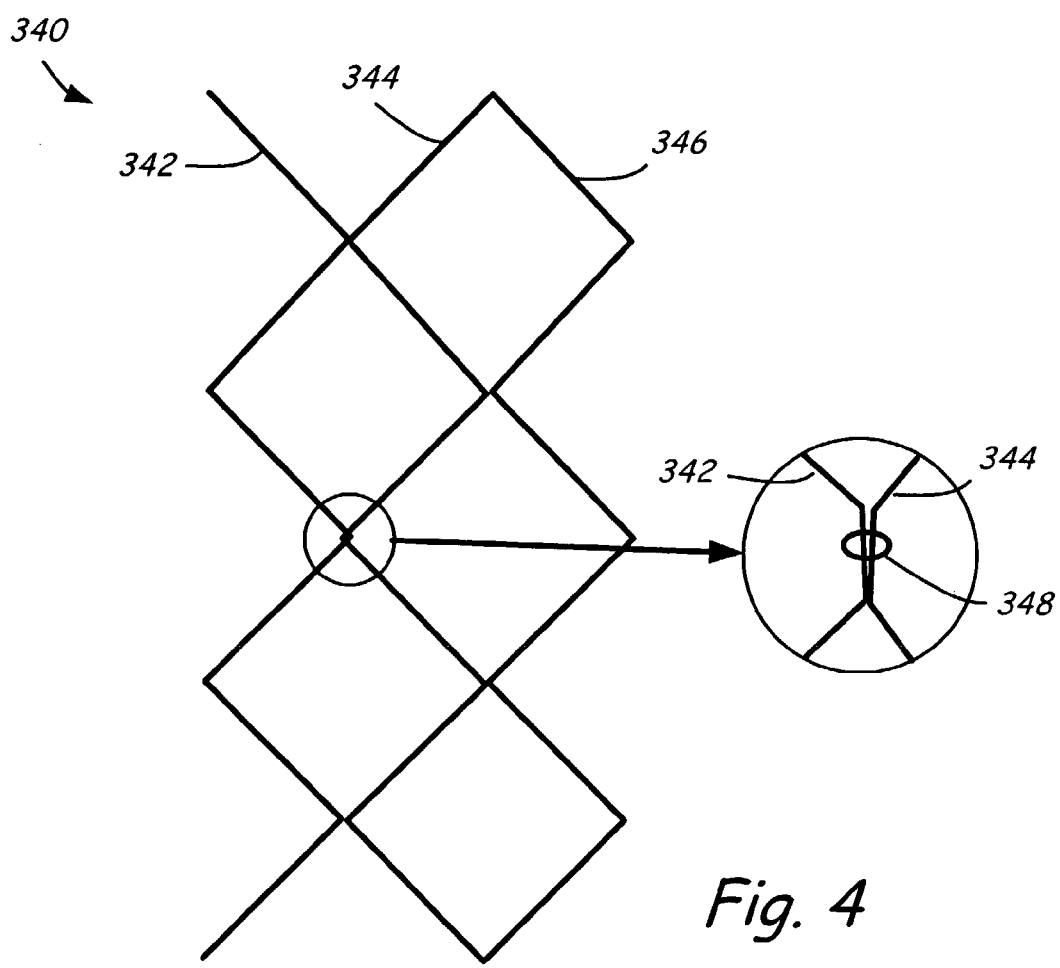
FIG. 4 is a top view of a portion of a stent that has been unfolded.

FIG. 4 illustrates an unfolded plan view, of a portion of a stent 340 according, to an alternative embodiment of the present invention. Rings 342, 344 and 346 extend axially along stent 340. Each of the rings 342, 344 and 346 are zigzag in shape and meet at various intersection points. Rings 342 and 346 are coated pith an insulating material. In another embodiment, rings 342 and 346 are made of a ceramic or polymeric material. As illustrated in FIG. 4B, at a point of intersection between ring 342 and 344, a suitable connector 348 may be used. Connector 348 may be a ring or a tube that holds rings 342 and 344 together.

Figure 5:
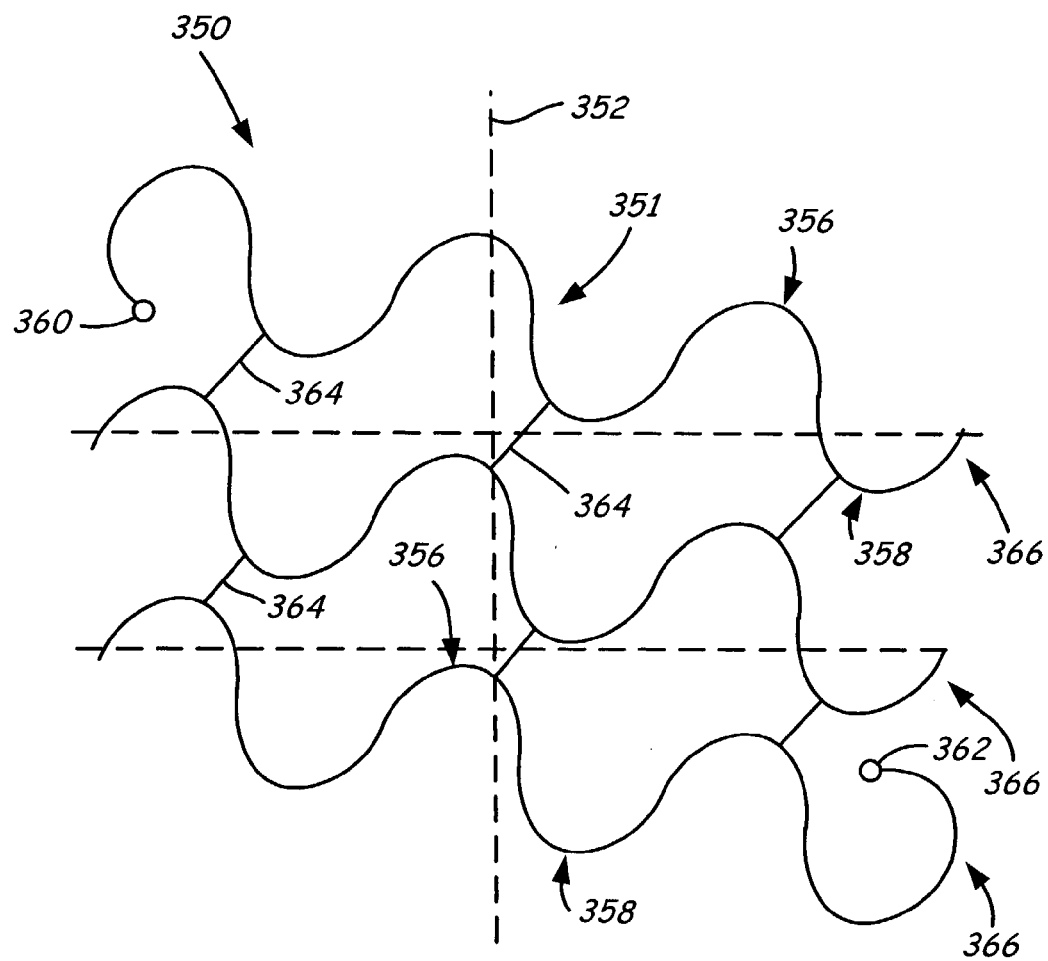
FIG. 5 is a top view of a stent that has been unfolded.

FIG. 5 illustrates an unfolded plan view of a stent 350 according to another embodiment of the present invention. Stent 350, when wrapped around a central axis 352, forms a generally tubular structure. Stent 350 includes an undulating ring 354 formed of a plurality of peaks 356 and troughs 358. If desired, ring 354 may be coated with an insulating material.

A pattern in undulating ring 354 is comprised of semicircular elements that support a greater surface area of a lumen. Other types of patterns may also be used. Ring 354 also includes free ends 360 and 362 that terminate at opposite ends of the stent and prevent the formation of electrical loops within tubular member 351.

Also, ring 354 is wound such that a plurality of rows 366 are formed in tubular member 351. In order to enhance the structural integrity of stent 350, connectors 364 are provided between rows 366 of ring 354. In order to prevent electrical loops from forming in tubular member 351, the connectors 364 are illustratively made of an insulating, material, such as a polymer or a ceramic. Alternatively, connector 364 may be a metal wire coated with an insulating material and connected between rows 366 so as to not make an electrical connection with ring 354.

In some instances, a radiopaque material is used on stents in order to enhance their visibility under x-ray procedures. Typically, a radiopaque metallic layer is applied to stents made of various polymers or ceramics that are non-radiopaque. The radiopaque layer typically distorts magnetic resonance images as discussed earlier. In order to prevent the formation of electrical loops in the radiopaque layer, a stent 370 similar to that shown in FIG. 6A may be used. Stent 370 forms a generally tubular structure 371 when in a deployed position, formed by a plurality of coil-shaped members 372. For each of the plurality of coil-shaped members 372, an insulating material, illustratively a polymeric or a ceramic material, is used to separate portions of a radiopaque layer to prevent electrical loops from being formed within the stent.

Figure 6A:
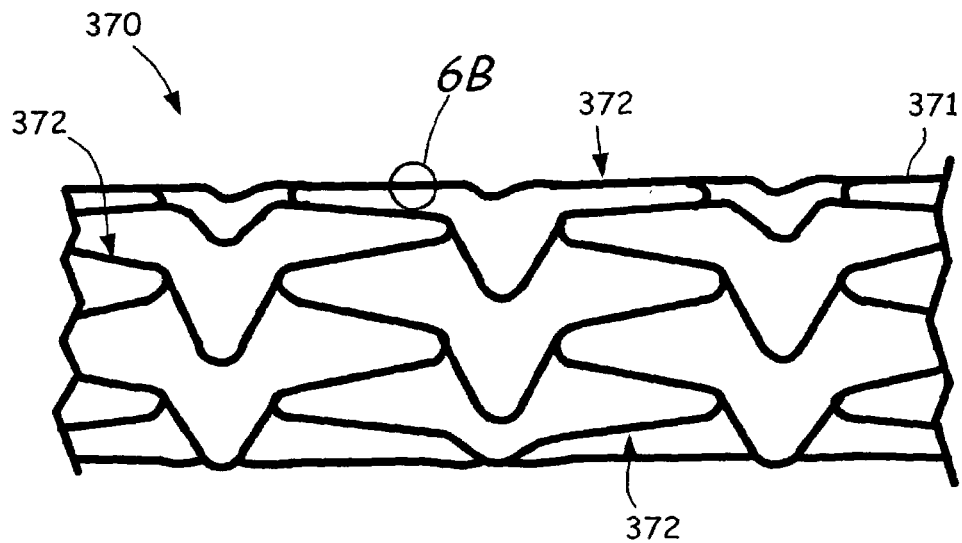
FIG. 6A is a side perspective view of a stent.
Figure 6B:
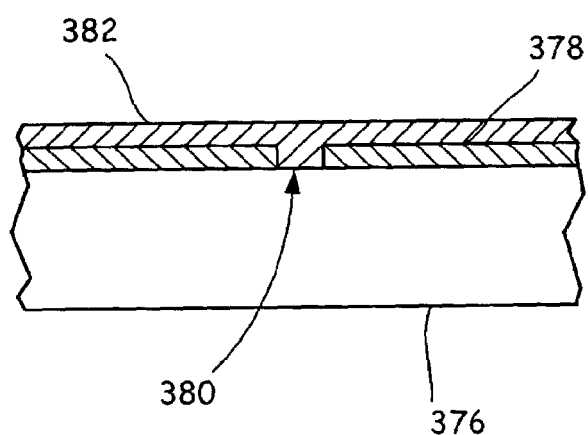
FIG. 6B is a cross-section of a portion of the stent illustrated in FIG. 6A.

FIG. 6B illustrates a cross section of a portion designated 6B of the stent in FIG. 6A. A base layer 376 is comprised of polymer or ceramic material. The radiopaque layer 378 is then applied to the polymer or ceramic connector. However, gaps 380 in the radiopaque layer may be made such that a polymer or ceramic top layer 382 can coat the radiopaque layer 378 and prevent any connections between portions of the radiopaque layer 378 by filling gaps 380 with insulating material. Thus, portions of the radiopaque layer 378 are spaced apart from each other by the insulating material in gaps 380. Gaps 380 can be made in the radiopaque layer by a masking procedure during a coating process or by laser ablation after the radiopaque layer has been deposited. Illustratively, each of the plurality of coil-shaped members includes at least one gap 380 formed in radiopaque layer 378, the gap being filled with insulating material.

Figure 7:
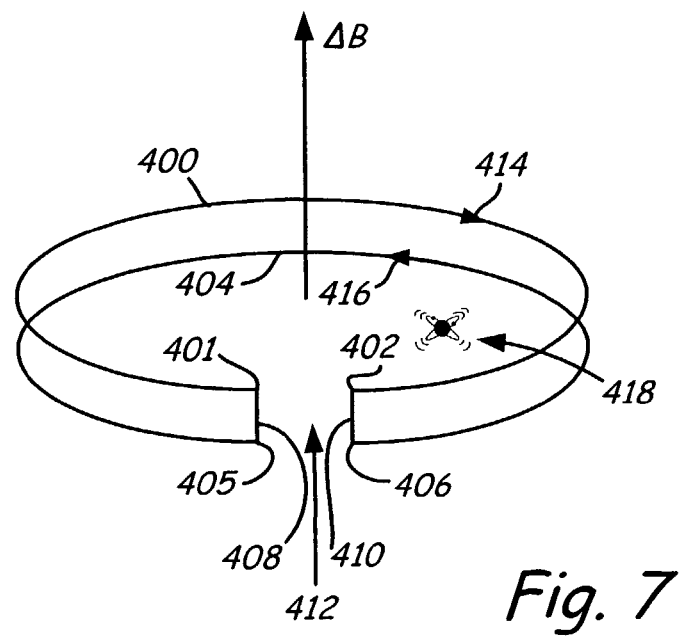
FIG. 7 is an illustration of two connected ring portions.

In an alternative embodiment, a design is chosen wherein rings of a stent are twisted in such a way that a current in one direction is counteracted by a current in the opposite direction. This is explained with regard to FIG. 7. FIG. 7 illustrates a first ring portion 400 having spaced apart ends 401 and 402 and a second ring portion 404 including spaced apart ends 405 and 406.

Each of the ring portions are connected to each other via connectors 408 and 410. Connector 408 connects end 401 of ring portion 400 to end 405 of ring portion 404. Connector 410 connects end 402 of ring portion 400 to end 406 of ring portion 404. Collectively, ring portions 400 and 404 are connected together to form a ring 411 having a gap 412 along a periphery of the ring 411.

Accordingly, when ring portions 400 and 404 are subject to a changing magnetic field represented as ΔB, current flowing in each of the ring portions 400 and 404 will be opposed, which is represented by arrows 414 and 416. This allows spins, for example spin 418, to be excited by RF source 140 and gradient generator 130. When used in a stent, a plurality of rings similar to ring 411 allows spins inside a tubular member of the stent to be excited.

Figure 8:
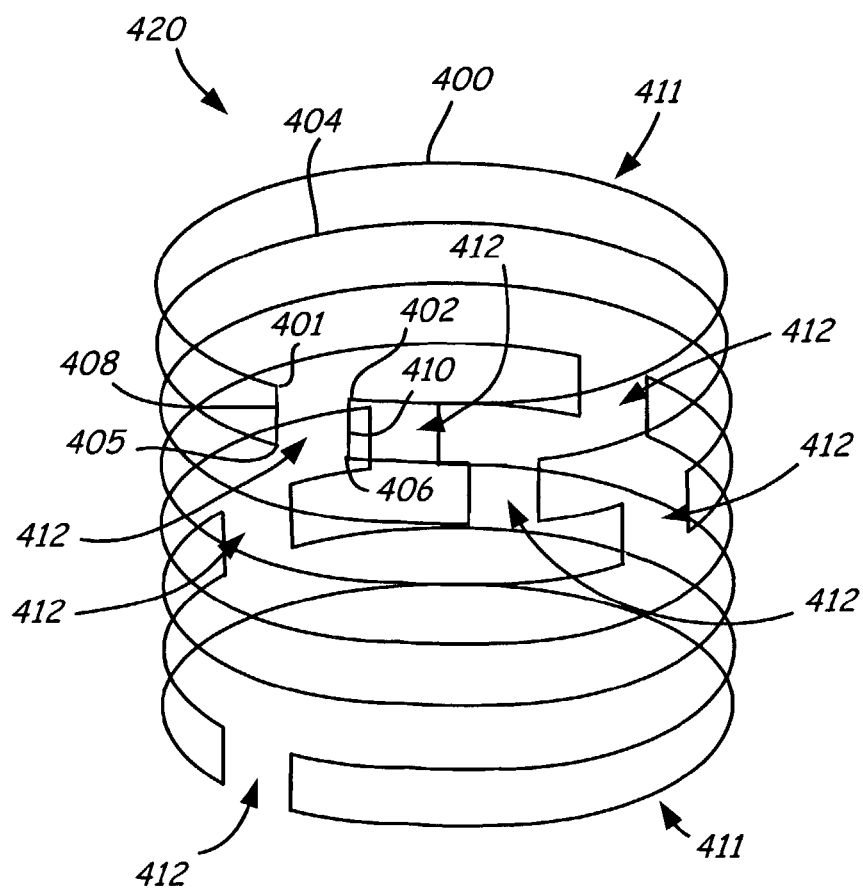
FIG. 8 is a perspective view of a stent having electrically opposed ring portions.

FIG. 8 illustrates a plurality of rings 411 connected together in a stent 420. The rings 411 include ring portions 400 and 404 as previously described. The ring portions 400 and 404 have spaced apart ends 401, 402 and 405, 406, respectively. Collectively, the ring portions of rings 411 define gaps 412 along an outer periphery of each of the rings 411. In order to improve the structural integrity of stent 420, gaps 412 can be spaced apart radially about the circumference of the tubular structure of the stent. In one embodiment, at least one of the gaps 412 is spaced apart radially from at least one of the other gaps 412 about the circumference of stent 420.

Figure 9A:
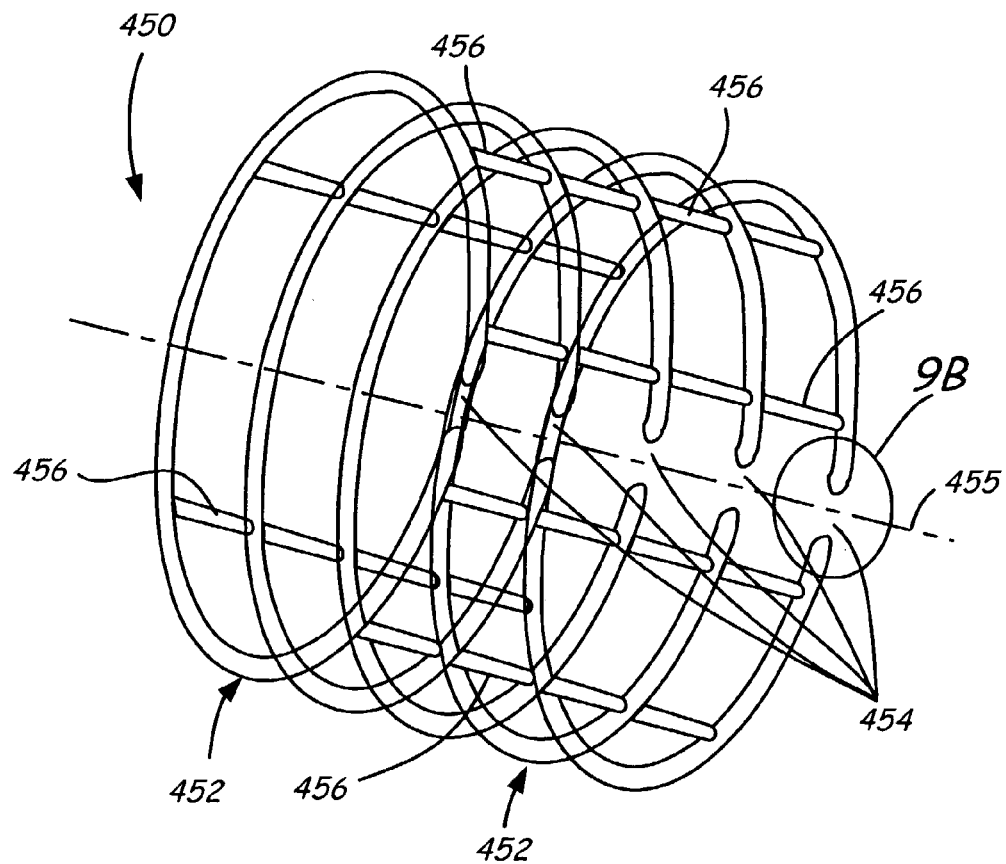
FIG. 9A is a perspective view of an alternative embodiment of a stent having electrically oppposed rings.
Figure 9B:
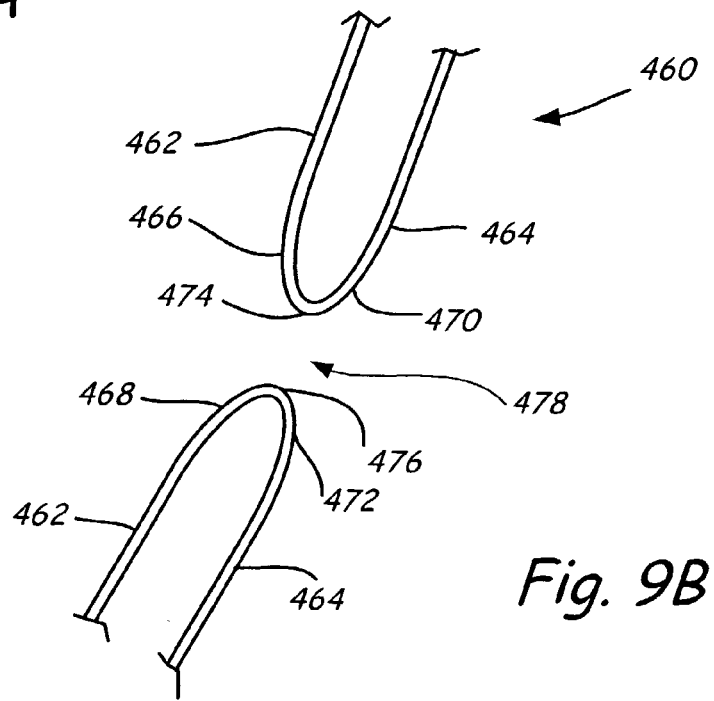
FIG. 9B is a portion of the stent in FIG. 9A.

Other embodiments having electrically opposed rings may be used. For example, a stent as shown in FIG. 9A may be used in magnetic resonance imaging. Since each of the currents generated in the rings are offset by a corresponding opposite current, the inside of the stent is visible during magnetic resonance imaging from various angles. Stent 450 includes a plurality of rings 452 similar to ring 411 illustrated, in FIG. 7. Each of the rings 452 has a corresponding gap 454 along a periphery of the stent 450 in an axial direction with respect to central axis 455. Accordingly, spins inside stent 450 are excited and the MRI visibility inside stent 450 is enhanced. The plurality of rings 452 are attached to each other by connectors 456. Illustratively, connectors 456 are made of an insulating material.

FIG. 7B illustrates a portion designated 8B of the stent in FIG. 7A. Ring 460 includes a first ring portion 462 and a second ring portion 464. Ring portion 462 has spaced apart ends 466 and 468 and ring portion 464 has spaced apart ends 470 and 472. Connector 474 connects end 466 to end 470 while connector 476 connects end 468 to end 472. Ring portions 462 and 464 also define a gap 478 along the outer periphery of ring 460. Each of the other rings 452 are constructed similarly to ring 460.

Insulating materials within the stents in the above examples can be various polymeric or ceramic materials. One such material is ePTFE (expanded polytetrafluoroethylene). Various ePTFE fibers, films and tubes can be purchased from Zeus Industrial Products of Orangeburg, S.C.; International Polymer Engineering of Tempe, Ariz.; and W. L. Gore & Associates, Inc. of Elkton, Md. The ePTFE materials are soft, microporous (herein various pore sizes of 0.2–3 microns), flexible and exhibit dielectric properties, strength and biocompatibility. Flexible films or fibers can be fabricated into connector stent connections and then heated to 372° C. for approximately 10 minutes. Consequently, the ePTFE connections are adhered together to form stent connectors. The heat treatments can be varied and are generally conducted 10° C. below the melting or degrading temperature of PTFE. The treatments increase the tensile strength of the ePTFE films, tubes or fibers. There are various other ways to fabricate ePTFE. For example, stent connectors can be connected by multiple layer tubes, then subjected to heat treatments. The ePTFE film can also be wrapped around stent connectors to make the connections.

Although the present invention has been described with reference to illustrative embodiments, workers skilled in the art will recognize that changes may be made in form and detail without departing from the spirit and scope of the invention.

What is claimed is:

1. A stent comprising;
   a generally tubular structure having a plurality of non conductive coil-shaped structural members;
   a radiopaque layer covering the coil shaped structural members, wherein each coil-shaped structural member defines a gap in the radiopaque layer; and
   a coating of insulating material applied to the radiopaque layer, wherein the coating of the insulating material is disposed in the gaps of the radiopaque layer to prevent the formation of an electrical loop across the gaps.

2. The stent of claim 1, wherein the insulating material is a polymeric material.

3. The stent of claim 1 wherein the structural members are selected from the group comprising ceramics and polymers.

4. A stent comprising:
   a generally tubular structure having a plurality of non conductive coil shaped structural members;
   a radiopaque layer applied to the coil shaped structural members, wherein each coil-shaped structural member defines a gap in the radiopaque layer; and
   a coating of insulating material applied to the radiopaque layer to prevent the formation of an electrical loop across the gaps,
   said radiopaque layer and said insulating material being adapted to allow magnetic changes in a region immediately proximate the generally tubular structure, induced by a magnetic resonance imaging process, to be substantially unobstructed by the generally tubular structure.

5. The stent of claim 4 wherein the generally tubular structure comprises a plurality of generally coaxially arranged ring connected to one another such that current induced in adjacent ring flows in opposite directions in the adjacent ring.

6. The stent of claim 5 wherein the ring structures comprise:
   a first ring portion including a first end and a second end spaced apart from the first end;
   a second ring portion including a first end and a second end spaced apart from the first end of the second ring portion;
   a first connector connecting the first end of the first ring portion and the first end of the second ring portion; and
   a second connector connecting the second end of the first ring portion and the second end of the second ring portion, wherein a current flows in a first direction in the first ring portion and in a second direction, opposite the first direction, in the second ring portion.

7. The stent of claim 6 wherein the first ring portion and the second ring portion are positioned substantially parallel to each other.

8. The stent of claim 6 wherein the first and second ring portions are made of a substantially non-ferromagnetic material.

9. The stent of claim 6 wherein the first ring portion and the second ring portion define a gap in an axial direction along an outer periphery of the generally tubular structure.

10. The stent of claim 5, wherein the generally tubular structure comprises:
    a plurality of rings, each ring compromising:
       a first ring portion disposed about a central axis and including a first end and a second end spaced apart from the first end;
       a second ring portion disposed about the central axis and including a first end and a second end spaced apart from the first end of the second ring portion;
       a first connector connecting the first end of the first ring portion and the first end of the second ring portion; and
       a second connector connecting the second end of the first ring portion and the second end of the second ring portion, wherein the first ring portion and the second ring portion define a gap in an axial direction along an outer periphery of the ring; and
    a plurality of connectors connecting the plurality of rings.

11. The stent of claim 10 wherein an induced current flows in a first direction around the central axis in the first ring portion and in a second direction, opposite the first direction, around the central axis in the second ring portion in each ring.

12. The stent of claim 10 wherein at least one of the gaps in the plurality of rings is spaced radially about a circumference of the generally tubular structure with respect to one other gap.

13. The stent of claim 4 wherein the plurality of electrically conductive structural members each have an overall conformation rendering the electrically conductive structural members electrically discontinuous.

14. The stent of claim 13 wherein the structural members comprise:
    a plurality of rings having an insulating material disposed thereon and spaced about a central axis of the generally tubular structure, the plurality of rings being spaced apart from each other by the insulating material.

15. The stent of claim 14 wherein the insulating material is a polymeric material.

16. The stent of claim 14 wherein the insulating material is a ceramic material.

17. The stent of claim 14 wherein each of the plurality of rings extend axially from a first end of the stent to a second end of the stent in a spiral conformation.

18. The stent of claim 17 wherein at least two of the rings intersect at an angle at an intersection point, and wherein at the intersection point, the insulating material from one of the at least two rings engages the insulating material from the other of the at least two rings.

19. The stent of claim 4 wherein the insulating material covers the radiopaque layer.

20. The stent of claim 4 wherein the structural members are selected from the group comprising ceramics and polymers.

* * * * *